United States Patent
Faff et al.

(10) Patent No.: US 6,174,672 B1
(45) Date of Patent: Jan. 16, 2001

(54) PROCESS AND TEST KIT FOR NON-RADIOACTIVE ENZYMATIC DETECTION OF REVERSE TRANSCRIPTASE

(75) Inventors: Ortwin Faff, Unterschleissheim; Alois Gabriel Hisem, Landshut, both of (DE)

(73) Assignee: Retro-Tech GmbH Gesellschaft fur Retrovirale Technologie, Unterschleibheim (DE)

( * ) Notice: Under 35 U.S.C. 154(b), the term of this patent shall be extended for 0 days.

(21) Appl. No.: 08/952,068
(22) PCT Filed: Mar. 4, 1997
(86) PCT No.: PCT/DE97/00391
 § 371 Date: Feb. 10, 1998
 § 102(e) Date: Feb. 10, 1998
(87) PCT Pub. No.: WO97/32995
 PCT Pub. Date: Sep. 12, 1997

(30) Foreign Application Priority Data

Mar. 6, 1996 (DE) .............................. 196 08 687

(51) Int. Cl.[7] .......................... C12Q 1/68; G01N 33/573; C12P 19/34; C07H 21/04
(52) U.S. Cl. .............................. 435/6; 435/7.4; 435/91.2; 435/91.21; 536/24.33; 536/25.4
(58) Field of Search .......................... 435/6, 91.2, 91.21, 435/7.4; 536/24.33, 25.4

(56) References Cited

U.S. PATENT DOCUMENTS 5,344,757 * 9/1994 Holtke et al. ............................ 435/6

FOREIGN PATENT DOCUMENTS

| 44 16 300 | 12/1994 | (DE) . |
| 0 392 459 | 10/1990 | (EP) . |
| 0 480 408 | 4/1992 | (EP) . |
| 04 148 698 | * 5/1992 | (JP) . |
| 04 267 898 | * 9/1992 | (JP) . |
| 04 187 099 | * 11/1996 | (JP) . |
| 90/06042 | 6/1990 | (WO) . |

OTHER PUBLICATIONS

Sharma et al. PCR–based construction of subtractive cDNA library using magnetic beads. Bio Techniques 15:610–612, Oct. 1993.*
Promega Protocols and Applications Guide, Promega Corporation, Third Edition, pp. 7 and 31–32, 1996.*
Journal of Virological Methods, vol. 41, No. 1, Jan. 1993, pp. 21–28, K. Suzuki, et al, "Colorimetric reverse transcriptase assay for HIV–1".

* cited by examiner

Primary Examiner—Karen Cochrane Carlson
Assistant Examiner—Devesh Srivastava
(74) Attorney, Agent, or Firm—Nixon & Vanderhye PC

(57) ABSTRACT

A method, and kit for carrying out the method, is provided for the non-radioactive and enzymatic detection of reverse transcriptase.

17 Claims, 5 Drawing Sheets

Test principle and protocol scheme of the reverse transcriptase assay

Test principle and protocol scheme of the reverse transcriptase assay

A - carrier plate
B - magnetic bars

Microtiter magnet separator for magnetic handling
of the particle-ligand complexes

| Reverse transcriptase concentration mU / test | Mean values of extinction at 405 nm | Standard deviation |
|---|---|---|
| Blank | 0.070 | ± 0.007 |
| 0.10 | 0.293 | ± 0.013 |
| 0.20 | 0.536 | ± 0.030 |
| 0.40 | 0.839 | ± 0.042 |
| 0.80 | 1.725 | ± 0.009 |
| 1.66 | 2.745 | ± 0.094 |
| 3.33 | 3.566 | ± 0.012 |
| 6.66 | 3.160 | ± 0.004 |

Table 1 : Reverse Transcriptase activity mean values of extinction after 60 min substrate incubation

PROCESS AND TEST KIT FOR NON-RADIOACTIVE ENZYMATIC DETECTION OF REVERSE TRANSCRIPTASE

PATENT SPECIFICATION

Process and test kit for non-radioactive, enzymatic detection of reverse transcriptase Virus diagnostics.

PRIOR ART

Currently, the routine detection of retroviruses is performed using the detection of virus-specific antibodies and/or viral components (antigens, RNA, proviral DNA), e.g. anti HIV antibody tests, HIV p24 antigen tests, HIV PCR detection test (Holodniy M. et al., J. Infect. Dis. 163, 862–866, 1991; Henrard DR et al., AIDS Res. Hum. Retrovir. 8, 47–52, 1992). However, this type of analysis is based on a non-functional or a structure-specific molecular interaction between antibody and antigen or PCR primer and proviral DNA, respectively, where no conclusions may be drawn with respect to the presence of a complete and a functional and intact virus. Furthermore, this type of analysis fails to cover all of the stages of a viral infection, e.g. the phase in which an infection has taken place but no antibodies have yet been formed. Thus, these factors sometimes lead to false-positive or negative results. For these reasons, it is urgently required to provide for direct and functional determination of retroviruses in biological samples. The medical and sociopolitical importance of retroviruses contributes further to this need, in particular in view of AIDS and a growing tendency and increasing role of retroviruses in animal and human diseases (leukemia, autoimmune diseases, cancer, etc.). Moreover, the transmission of retroviruses by infections causes severe problems in transfusion and transplantation medicine or otherwise requires qualitative examinations regarding viral contaminations in samples of lymph, saliva, sperm or blood of donors as well as in organs, skin, bone marrow, etc. destined for transplantation. The same problems of viral contamination or infection, respectively, apply to the use of biopharmaceuticals and other biotechnological or genetechnological preparations of biological origin used for therapeutical purposes in humans and animals as well as in medical basic reasearch. A prerequisite to solve the problems mentioned above is the direct and functional detection of retroviruses by means of methods which are reliable, sensitive, and as simple as possible.

Up to now, the direct and biologically functional detection of retroviruses was carried out successfully only in single cases and has been associated with a very high amount of work and time involved by infecting cells and has been possible only in purified viral preparations or in cell culture supernatants. So far, no quantitative, simple and reliable routine methods for the detection of retroviruses exist. A reason for this may be the complex composition of biological samples (blood, organic extracts, etc.) containing proteins, enzymes, vitamins, lipids, sugars, and various inhibitors. These complicate or prevent the direct and functional detection of retroviruses.

Reverse transcriptase is the key enzyme of all retroviruses carrying out the reverse transcription (translation) of viral RNA into complementary DNA (cDNA) and enabling the subsequent integration thereof into the genome of the host cell. The enzyme is retrovirus-specific and its enzyme activity indicates the existence of viral particles as well as their functional integrity since the enzyme is very unstable as a free molecule and is rapidly inactivated.

Although up to now a variety of tests to detect reverse transcriptase have been developed, these technologies failed to establish themselves as a routine method in virological and clinical diagnostics because of the following shortcomings:

a) use of radiolabeled components (substrates labeled by tritium, phosporus) and of health hazardous or enviromentally harmful organic solvents (trichloroacetic acid, toluene);

b) insufficient sensitivity of the non-radioactive methods as compared to ELISA (enzyme-linked immunoadsorbent assay) and PCR (polymerase chain reaction) technology because of the use for labeling and detection of the reaction products (cDNA) of antigen/antibody systems (i.e. digoxigenin/anti-digoxigenin; fluorescein/anti-fluorescein) having relatively low binding constants (Eberle, J. et al., J. Virol. Meth. 20, 347–356, 1992; K. Suzuki et al., J. Virol. Meth. 41, 21–28, 1993);

c) complicated routine handling and performance of kinetic measurements because of insufficient methods for the separation of reaction educts from products caused by double labeling of the newly synthesized cDNAs (membrane adsorption, filtration or capturing on a solid phase, respectively) (Eberle J. et al., J. Virol. Meth. 20, 347–356, 1992; K. Suzuki et al., J. Virol. Meth. 41, 21–28, 1993);

d) inefficient immobilization of the primers on solid phases (plastic) (T. Urabe et al., J. Virol, Meth. 40, 154–154, 1992).

The present method applying for grant of patent describes the direct and enzymatic routine detection of retroviruses using reverse transcriptase.

Solution of the Problem

The method to be patented and the corresponding test kit are based on the use in the reverse transcriptase reaction of a primer-and-template immobilized on magnetic particles in the form of a particle-primer/template complex (PPT complex) and labeling of the cDNA which is newly synthesized on the PPT complex by biotinylated deoxynuclectide triphosphates in the form of a PPT-cDNA complex and the detection thereof by streptavidin-coupled marker enzymes and appropriate substrates in the form of a PPT-cDNA-conjugate complex (see FIG. 2).

Magnetic particles and ligand complexes immobilized on those particles have the advantage that they may be separated from solutions as a solid phase in the presence of a magnetic field and may again be dispersed in solution in the absense of a magnetic field or by agitation, respectively (see FIG. 1). This simple, very quick, efficient, and reproducible physical process may upon immobilisation of molecules on magnetic particles be used in biological tests for the processing of these molecules and, if necessary, for their successive separation (immobilisation) and dispersion (solubilisation). This alternating magnetic treatment (FIG. 1) is particularly advantageous in enzymatic or biochemical reactions where reaction educts (substrates) have to be partially separated from products. The magnetic treatment of particle-ligand complexes in solution is effected by successive introduction and removal of magnets into and out of the proximity of the reaction vessel or the solution, respectively, whereby alternating separation and dispersion of the complexes or solution changes, washing, reaction stop etc. may be performed (FIG. 1). In microtiter plates, a so-called microtiter magnet separator (FIG. 3) consisting of an optically transparent carrier plate is employed for magnetic treatment which has 24 bar magnets introduced into the external space of the microtiter wells and, thus, separates the particle-ligand complexes present in solution onto the side walls of the wells (FIG. 1), thereby enabling solution changes, washing, and photometric measurements in the presence and without loss of the magnetic particle-ligand complexes to be conducted without any problems.

The method or test kit, respectively, to be patented uses magnetic particles having an immobilized primer-and-template which is necessary for the reverse transcriptase reaction. As primers, there may be employed a homo- or heterooligodeoxynucleotide triphosphate (e.g. oligo dT, oligo dG) while as a template (matrix RNA molecule) a homo- or heteropolymeric RNA such as poly rA (polyadenosine triphosphate) may be used. Particles, primer, and template together form the so-called particle-primer/template-complex reagent (PPT reagent). In the presence of reverse transcriptase and biotin-labeled as well as unlabeled deoxynucleotide triphosphates dNTP's the corresponding cDNA is synthesized complementary to the template RNA which is also immobilized on the magnetic particles by means of the template-primer and forms the so-called PPT-cDNA complex.

Excess non-incorporated nucleotides are washed off, and afterwards the biotinylated PPT-cDNA complex is incubated with streptavidin-conjugated marker enzymes (e.g. peroxidase, alkaline phosphatase), and the so-called PPT-cDNA-conjugate complex is formed. The excess of unbound streptavidin conjugate is washed off, and the marker enzyme immobilized onto the particles is incubated with the appropriate substrates (such as orthophenylenediamine, AEBTS, TMB), and the reaction is determined quantitatively by photometry using extinction/absorption or by luminometry.

The newly synthesized cDNA is labeled by biotin-dNTP's incorporated therein. An advantage of the biotin label is its very sensitive detection with streptavidin/avidin and a conjugated marker enzyme since biotin/streptavidin exhibit very strong binding ($10^{-15}$ M) in comparison to the relatively weak antigen/antibody binding ($10^{-7}$–$10^{-11}$ M). The method and test kit of the present invention provides for the non-radioactive, enzymatic detection of reverse transcriptase, characterized in that the method and test kit use a particle-primer/template complex (PPT complex) which may be magnetically successively separated and dispersed in combination with biotin labeling of the newly synthesized cDNA in a magnetizable PPT-cDNA complex and subsequent detection by means of streptavidin/avidin-conjugated marker enzymes (peroxidase, alkaline phophatase) and in a magnetizable PPT-cDNA-conjugate complex after addition of appropriate substrates.

The very efficient and simple magnetic handling of the particle-ligand complexes in combination with the extremely strong binding of the biotin/streptavidin system for the first time provides a method with a substantially improved sensitivity (0.1 mU* reverse transcriptase/test) corresponding to an at least tenfold increase as compared to other existing methods and products. Upon longer incubation, the sensitivity may even be enhanced up to 0.05 mU achieving a detection limit of approx. 10 pg reverse transcriptase per test with a specific activity of about 5000 Units/mg. In addition, because of the strong binding of the biotin/streptavidin system considerably less labeled substrate (e.g. biotin-dUTP) may be used whereby the linear range of the measurement increases over two orders of magnitude (approx. 0.5–10.0 mU/test).

The improved sensitivity, extended linear range as well as the easy, fast, and efficient handling render the novel method and test kit considerably attractive for clinical routine virus diagnostics of diseases as well as for the quality control of biopharmaceuticals.

The method of the present invention is characterized in that the test kit resulting from the method has the following composition:

a. PPT reagent-magnetic particle-primer/template reagent containing oligo dT with poly (rA) or RNA, respectively, or oligo dG with poly (rC) or RNA, respectively, or oligo (dC) with poly (rG) or RNA, respectively, in storage buffer consisting of PBS, triton X-100, EDTA, RNAse inhibitors and rt cryoprotection reagent;

b. PPT washing buffer containing Tris/HCl, pH 8.0; NaCl; EDTA;

c. virus lysis buffer containing Tris/HCl, pH 7.5; EDTA; triton X-100; NP-40; DTT;

d. nucleotide mixture containing dTTP with biotin-dUTP or dCTP with biotin-dCTP or dATP+dGTP+dTTP with biotin-dUTP or biotin-dCTP;

e. rt reaction buffer containing Tris/HCl, pH 8.0; KCl; $MgCl_2$;

f. rt washing buffer containing PBS and tween;

g. conjugate buffer containing washing buffer with rt blocking reagent;

h. streptavidin reagent containing unconjugated streptavidin or avidin;

i. conjugate reagent containing streptavidin or avidin conjugated to marker enzymes such as peroxidase, alkaline phosphatase, or containing biotin conjugated to marker enzymes;

j. substrate containing the appropriate conjugated marker enzyme substrate such as 2,2'-azido bis(3-ethylbenzthiazoline-6-sulphonic acid), diammoniuim salt;

k. substrate buffer containing the appropriate buffer for the above conjugated marker enzyme substrates such as $Na_2HPO_4$, $NaBO_2$ and citric acid pH 4.5;

l. reference enzyme containing HIV reverse transcriptase as a marker.

The particle-primer/template complex (PPT complex) of the present invention is composed of magnetic particles (e.g. DYNAL, IGI, BIO MAG, ADVANCED BIOTECHNOLOGIES, NOVAGE) with reaction primer and reaction template immobilized thereon. *Definition of the reverse transcriptase unit: one unit is the enzyme activity leading to incorporation of 1.0 nmol [$^3$H]-TMP into acid precipitable products within 10 min at 37° C. using poly (A)/(dT)$_{15}$.

Advantages of the Method/Test Kit

Compared to already existing detection methods and products, the method described and the corresponding test kit have the following advantages:

a) non-radioactive method/test kit or use of exclusively non-radioactive and aqueous reagents, respectively, avoidance of organic solvents (TCA, toluene, etc.), therefore practicable in any laboratory without specific authorization and environmetally friendly because radioactive and organic waste is avoided;

b) 10× improved sensitivity and increase of the linear measuring range (0.7–7.0 mU) as compared to other non-radioactive methods since biotin/streptavidin which is characterized by a very high binding constant is used as a marker system;

c) for the first time kinetic and inhibition studies may be performed in the non-radioactive range since the reverse transcription can be stopped by aspiration of the reaction mix;

d) simple and time-saving handling (max. 3 hours) by employment of magnetic separation and dispersion of particle-bound reaction educts/products;

e) for the first time repeated substrate additions and extinction measurements are possible in a reverse transcriptase assay because of magnetic immobilisation of the PPT-cDNA-conjugate complex;

f) high test capacity and may be performed routinely since practicable in microtiter format;

g) the method can be used universally for all species of retroviruses and reverse transcriptase, respectively, if appropriate specific reaction conditions are employed, and may be appropriately adapted and optimized;

h) detection of retroviruses is performed not only on a structural basis as in antigen/antibody or PCR/DNA tests but also biochemically functional using reverse transcriptase.

Fields of Use

Potential uses of the method and test kit are directed to the following areas:

a) Research & development laboratories in industry, universities, and major research institutes working in the development of antiviral agents, therapeutics, virus diagnostics, vaccines, experimenting models, etc. For all this work the direct detection of retroviruses is absolutely required.

b) Medical diagnostics and course control of retrovirus-caused diseases such as AIDS, leukemia, autoimmune diseases, cancer. The same applies to retrovirus-caused diseases in animals. Accordingly, potential users may be: clinics and hospitals, blood banks as well as clinical laboratories and laboratory associations.

c) Transplantation and transfusion medicine as a whole as well as donor banks of blood, organs, bone marrow, sperm, etc. The detection of a retroviral contamination in the above-mentioned donor materials is extraordinarily important to prevent spreading and infections by transplantation or donation.

d) Biological quality control and approval of biopharmaceuticals (e.g. blood derivatives, coagulants), bio/genetechnologically manufactured cosmetics, food stuffs and laboratory reagents (e.g. cell cultures, immunoglobulins, therapeutic enzymes, insulin, fetal sera, etc.) which have to be examined with respect to retroviruses to prevent their possible transmission.

Table 1 shows reverse transcriptase mean valves of extinction after 60 min substrate incubation.

EXAMPLE

To develop and optimize the method, HIV reverse transcriptase was used as a model enzyme. The following experimental steps were performed per each test sample (well):

1) 50 $\mu$l of particle-primer/template reagent (oligo dt/poly rA-magnetic particles) were introduced and diluted with 150 $\mu$l of particle washing buffer.

2) In the presence of the microtiter magnetic separator, the particles were collected on the side wall of the well for 5 minutes, the solution was aspirated with an 8 channel washing device and subsequently washed with 3×200 $\mu$l of particle washing buffer.

3) After aspiration of the particle washing buffer 20 $\mu$l of HIV reverse transcriptase in different concentrations in lysis buffer consisting of 10 mM Tris-HCl, pH 7.5, 5 mM DTT, 0.5% NP40, 0.5% triton X-100, 2.5 mM EDTA was introduced and mixed with particle-template/primer reagent. Alternatively for inhibition studies 10 $\mu$l of enzyme and 10 $\mu$l of inhibitor in the above lysis buffer may be introduced.

4) The reaction was started by addition of 30 $\mu$l reaction mix and incubated for 60 min at 37° C. and agitated in a reaction mixture made of 10 $\mu$M dTTP+biotin-dUTP, 50 mM Tris-HCl, pH 8.0, 80 mM KCl, 10 mM MgCl$_2$, 2 mM DTT, 1 mM EDTA, 0.2% NP40, 0.2% triton X-100.

5) The reaction was stopped by separation of the magnetic particles and aspiration of the reaction mixture, and the particles with the reaction product (cDNA) immobilized thereon were washed in 5×200 $\mu$l of washing buffer consisting of phosphate-buffered saline (PBS) with 0.1% tween.

6) Afterwards the particles were incubated for 30 min at 37° C. With 150 $\mu$l streptavidin-peroxidase in conjugate buffer and were mixed.

7) Excess unbound streptavidin-peroxidase was then aspirated as described and the particles were washed in 5×200 $\mu$l of washing buffer.

8) Then, 200 ml AEBTS substrate in substrate buffer were added and kinetic measurement of the extinction of the developing green colour was performed at 405 nm and at a reference wave length of 492 nm.

Figure 1:
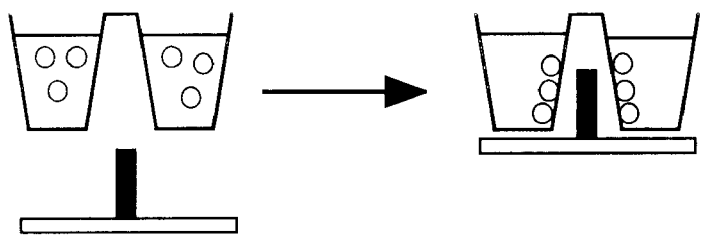
FIG. 1 shows a schematic of the magnetic handling of the particle-ligand complexes.
Figure 1:
Figure 2:
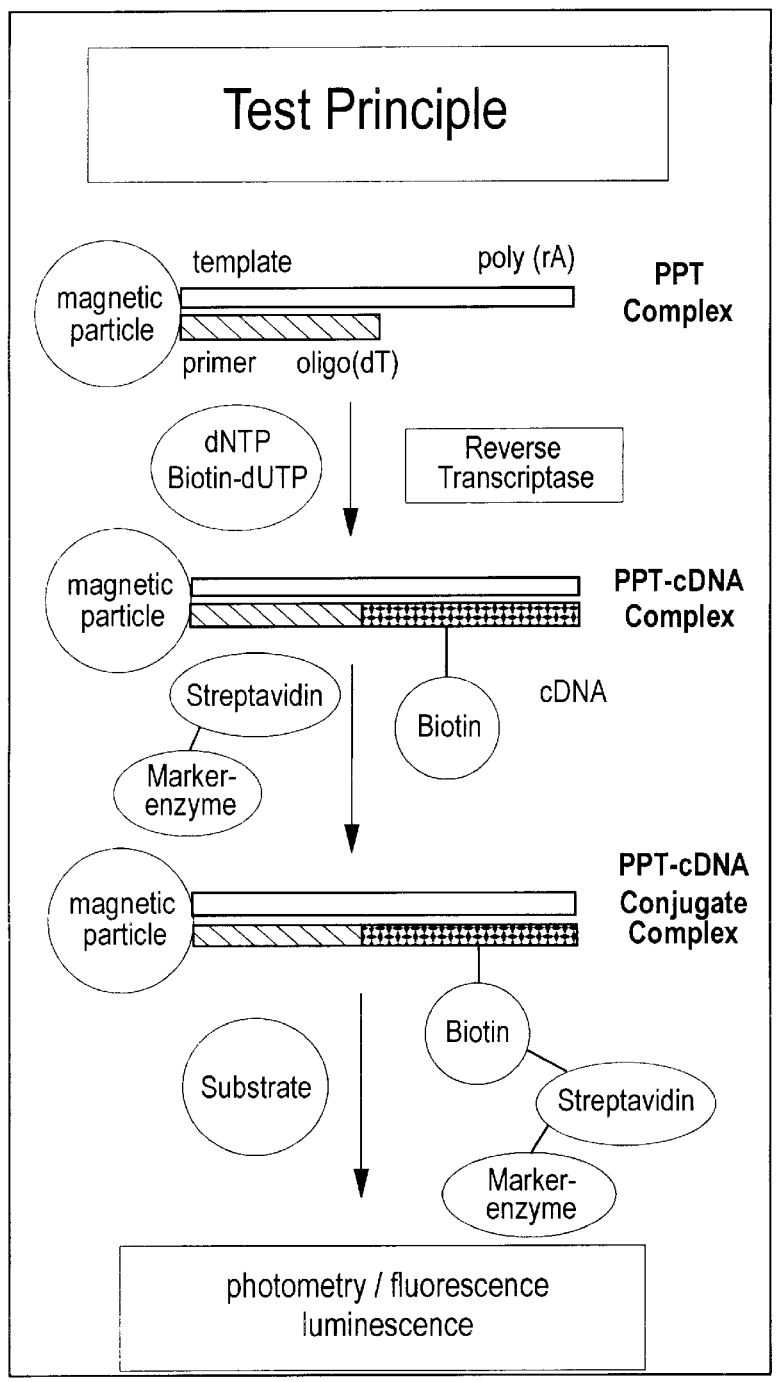
FIG. 2 shows the test principle and protocol scheme, of the reverse transcriptase assay.
Figure 3:
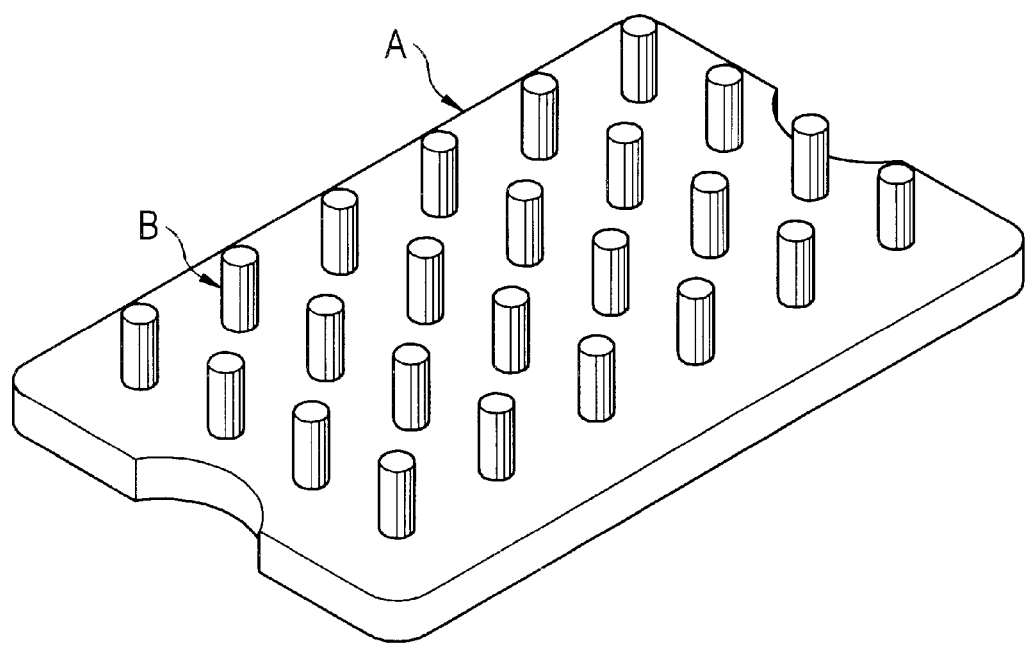
FIG. 3 shows a microtiter magnet separator for magnetic handling of the particle-ligand complexes with a carrier plate and magnetic bars.
Figure 4:
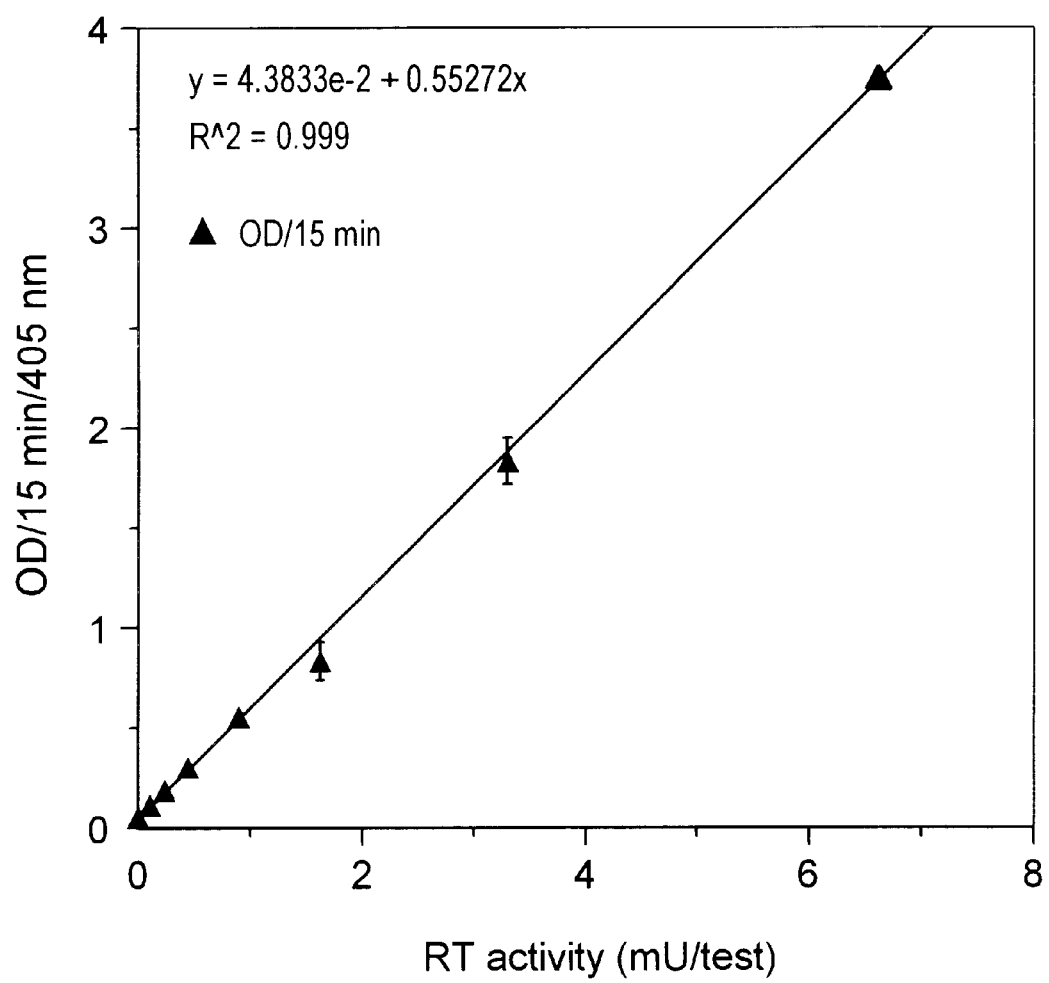
FIG. 4 shows a standard curve of HIV reverse transcriptase activity of OD/15 min/405 nm versus RT activity (mU/test).

The values of FIG. 4 and Tab. 1 show a linear increase of the extinction or the enzymatic activity, respectively, in a range of 0.1–7.0 mU of reverse transcriptase within a period of 15 min after addition of the substrate. Prolonging the incubation period with substrate to 60 min the sensitivity may be lowered down to approx. 0.05 mU.

TABLE 1

Reverse Transcriptase activity mean values of extinction after 60 min substrate incubation

| Reverse transcriptase concentration mU/test | Mean values of extinction at 405 nm | Standard deviation |
| --- | --- | --- |
| Blank | 0.070 | ±0.007 |
| 0.10 | 0.293 | ±0.013 |
| 0.20 | 0.536 | ±0.030 |
| 0.40 | 0.839 | ±0.042 |
| 0.80 | 1.725 | ±0.009 |
| 1.66 | 2.745 | ±0.094 |
| 3.33 | 3.566 | ±0.012 |
| 6.66 | 3.160 | ±0.004 |

What is claimed is:

1. A method of non-radioactive, enzymatic detection of reverse transcriptase in a sample, said method comprising preparing a complex of a magnetic particle and a primer/template immobilized thereon;

preincubating said complex with said sample;

adding at least one non-radioactively labeled deoxynucleotide triphosphate and unlabeled deoxynucleotide triphosphate and incubating said mixture under conditions where a labeled complex-cDNA combination is synthesized in the presence of reverse transcriptase in said sample; and detecting said labeled complex-cDNA combination.

2. The method of claim 1 wherein said labeled complex-cDNA combination is collected by means of an external magnetic field.

3. The method of claim 1 wherein said template is RNA.

4. The method of claim 1 wherein the primer is DNA.

5. The method of claim 4 wherein the primer is selected from the group consisting of oligo (dT), oligo (dG), oligo (dC), oligo (dA), a heteropolymer mixture of at least two of d(T), d(G), d(C) and d(A), and a mixture thereof.

6. The method of claim 3 wherein the template is selected from the group consisting of poly(rA), poly (rC), poly (rG), natural RNA and a combination thereof.

7. The method of claim 1, wherein that label is selected from the group consisting of biotin, Br (bromide), digoxigenin and fluorescent labels.

8. The method of claim 1 wherein said labeled deoxynucleotide triphosphate is a biotinylated deoxynucleotide triphosphate.

9. The method of claim 1 wherein said template is a homopolymer or heteropolymer.

10. The method of claim 1 wherein said primer is a homopolymer or heteropolymer.

11. The method of claim 7 wherein said biotin label is detected with an avidin or streptavidin coupled enzyme marker and a corresponding substrate.

12. The method of claim 1 wherein a photometer, a fluorimeter or a luminometer is used for said detection.

13. The method of claim 1 wherein said sample is a biological sample.

14. The method of claim 13 wherein said sample is selected from the group consisting of a patient sample and a cell culture supernatant.

15. The method of claim 1 wherein said labeled complex-cDNA combination is collected by means of a permanent magnet separator comprising an optically transparent holder plate and magnetic rods entering the external space between the sample containing wells.

16. The method of claim 11 wherein said enzyme marker is selected from the group consisting of peroxidase and alkaline phosphatase.

17. A kit comprising a complex of a magnetic particle and a primer/template immobilized thereon, at least one reaction buffer a non-radioactively labeled deoxynucleotide triphosphate and an unlabeled deoxynucleotide triphosphate.

* * * * *